US008128576B2

(12) United States Patent
Tracey et al.

(10) Patent No.: US 8,128,576 B2
(45) Date of Patent: Mar. 6, 2012

(54) SYSTEM AND METHOD FOR URODYNAMIC EVALUATION UTILIZING MICRO ELECTRO-MECHANICAL SYSTEM TECHNOLOGY

(75) Inventors: Michael R. Tracey, Branchburg, NJ (US); Anthony DiUbaldi, Jackson, NJ (US); Stephen Wahlgren, Easton, PA (US); Rex O. Bare, Lake Forest, CA (US); Bradley J. Sargent, Mission Viejo, CA (US)

(73) Assignee: Ethicon, Inc., Somerville, NJ (US)

( * ) Notice: Subject to any disclaimer, the term of this patent is extended or adjusted under 35 U.S.C. 154(b) by 1028 days.

(21) Appl. No.: 11/635,403

(22) Filed: Dec. 7, 2006

(65) Prior Publication Data

US 2008/0139875 A1    Jun. 12, 2008

(51) Int. Cl.
*A61B 5/00* (2006.01)
*A61B 1/307* (2006.01)

(52) U.S. Cl. .................... 600/561; 600/300; 600/135
(58) Field of Classification Search ................ 600/561, 600/135, 29–32, 300, 301, 372–397, 591; 606/151, 153, 155, 156
See application file for complete search history.

(56) References Cited

U.S. PATENT DOCUMENTS

| | | | | |
|---|---|---|---|---|
| 4,606,329 A | * | 8/1986 | Hough | 600/25 |
| 4,669,478 A | * | 6/1987 | Robertson | 600/300 |
| 4,901,735 A | * | 2/1990 | von Berg | 600/561 |
| 5,167,237 A | | 12/1992 | Rabin et al. | |
| 6,167,886 B1 | * | 1/2001 | Engel et al. | 128/885 |
| 6,398,718 B1 | * | 6/2002 | Yachia et al. | 600/29 |
| 6,656,194 B1 | * | 12/2003 | Gannoe et al. | 606/153 |
| 7,076,284 B2 | * | 7/2006 | Segawa et al. | 600/424 |
| 2002/0082551 A1 | * | 6/2002 | Yachia et al. | 604/103.01 |
| 2004/0082850 A1 | * | 4/2004 | Bonner et al. | 600/424 |
| 2005/0177067 A1 | * | 8/2005 | Tracey et al. | 600/561 |
| 2007/0244373 A1 | * | 10/2007 | Osypka | 600/301 |

FOREIGN PATENT DOCUMENTS

| | | |
|---|---|---|
| WO | WO 2005/077276 A | 8/2005 |
| WO | WO 2005/110205 A | 11/2005 |
| WO | WO 2005/115245 A | 12/2005 |

OTHER PUBLICATIONS

International Search Report dated Apr. 23, 2008.

* cited by examiner

*Primary Examiner* — Max Hindenburg
*Assistant Examiner* — John Pani

(57) ABSTRACT

An implantable urodynamic system includes an implantable first device deployable in a patient's bladder, an implantable second device deployable in a patient's vaginal canal, and a data acquisition and analysis module or processing unit external to the body of the patient. The first device includes a magnet and an inductive coil, and the second device includes a magnet, an inductive coil and a battery. When deployed in the patient's body, attraction between the magnets maintains the two devices in close proximity to one another to effect an inductive coupling between the coils so that the first device may be powered by the battery of the second device. The urodynamic system is intended to facilitate measurement, collection, and wireless transmission of real-time, or near real-time, data (bladder pressure, abdominal pressure, and temperature) from an ambulatory patient. This data is of value in diagnosing a number of abnormal bladder conditions, such as infection, overactive bladder, bladder spasms, and the like.

21 Claims, 12 Drawing Sheets

SYSTEM AND METHOD FOR URODYNAMIC EVALUATION UTILIZING MICRO ELECTRO-MECHANICAL SYSTEM TECHNOLOGY

BACKGROUND OF THE INVENTION

1. Field of the Invention

The present invention relates generally to devices and methods for urodynamic evaluation, and more particularly, to such a system and method that utilizes micro-electronic mechanical system (MEMS) technology.

2. Description of the Prior Art

In order to treat urinary incontinence, it must first be understood which type of incontinence the patient is suffering from, and the physical causes for the incontinence. Many types of urodynamic systems and tests are currently available to try to assess the type and causes of incontinence. These systems can be broadly categorized in two ways: office based systems and ambulatory systems.

Office based systems are designed for use in a doctor's or clinician's office. Many of these systems involve invasive testing using catheters and the like. Ambulatory systems are designed to capture data outside the office over a longer period of time, such as 1-2 days.

Known ambulatory systems for urodynamic measurements are also invasive in that they use catheters to capture pressure data within the urethral tract or in the bladder. It is readily apparent that such known ambulatory systems are uncomfortable and invasive for the patient. Further, because the catheters are inter-dwelling, they are prone to movement or migration over time as the patient moves around. In addition, they may not accurately capture typical daily occurrences, as the patient is, due to the discomfort, prone to move less and engage in fewer activities than normal while undergoing the assessment. Finally, the invasive catheters may also interfere with true physiological responses, as they can irritate the internal tissues/organs through which they are inserted. Thus, migration of the pressure sensors and their invasive nature limits the reliability and usefulness of the data. Another ambulatory system describes implanting a device within the bladder of the patient, but retrieval of the device can be an issue.

U.S. patent application Ser. No. 11/043,830, filed on Jan. 26, 2005, having Michael R. Tracey and Anthony DiUbaldi as the named inventors, and entitled "System and Method for Urodynamic Evaluation Utilizing Micro-Electronic Mechanical System", and further being published on Aug. 11, 2005 and being assigned Publication No. US2005/0177067A1, the disclosure of which is incorporated herein by reference, describes an implantable urodynamic system for implanting within a patient's body. It includes two implantable devices. The first device, sized for implantation within a patient's bladder, includes a power source, at least one sensor for sensing a physiological property within the bladder, and a data storage element for storing data representing the physiological property sensed by the sensor. The first implantable device also includes a collapsible housing. The collapsible housing has a collapsed configuration sized for insertion through the patient's urethra and into the patient's bladder, and an expanded configuration sized for insertion within the bladder, but to prevent its passage from the bladder into the urethra.

The system can also have a second implantable device sized for implantation within the patient's vagina. This device also has a power source, at least one pressure sensor for sensing pressure within the vaginal canal, and a data storage element. In addition, it has a data retrieval device for retrieving and manipulating data from the first and second data storage elements once the devices are removed from the body. This second implantable device is encapsulated within a pliable casing, such as cotton, dimensioned to hold the device against the vaginal walls.

OBJECTS AND SUMMARY OF THE INVENTION

It is an object of the present invention to provide an implantable urodynamic system formed of components which are deployable in a patient's bladder and vaginal canal and which are structured and cooperate to facilitate the retrieval of the components therefrom.

It is another object of the present invention to provide an implantable urodynamic system having components deployable in a patient's body which remain properly positioned therein without migration in the patient's body.

It is yet a further object of the present invention to provide an implantable urodynamic system which senses a physiological property or properties within a patient's body and minimizes or eliminates the possibility of erroneous measurements being made.

It is a further object of the present invention to provide a urodynamic evaluation system for measuring a physiological property of a patient while the patient remains ambulatory.

It is still a further object of the present invention to provide an implantable urodynamic system having components which may be implanted in a patient's body for relatively long periods of time.

It is yet another object of the present invention to provide a system and method for urodynamic evaluation which utilizes micro electro-mechanical system (MEMS) technology and which further overcomes inherent disadvantages associated with conventional office-based urodynamic systems and ambulatory systems.

In accordance with one form of the present invention, a urodynamic system, preferably constructed using MEMS technology, includes a first implantable device and a second implantable device.

The first implantable device, which is preferably sized to be placed in a patient's bladder, is inductively coupled and powered by the second implantable device via a magnet and coil situated on one end of the first implantable device. The first implantable device further has a sensor on an opposite end. The bladder implantable device is used to acquire patient bladder pressure data, or alternatively, temperature data, which are used for the diagnosis and treatment of bladder function, with the expressed purpose of allowing the patient to remain ambulatory. This device may include other functions and sensors, for example, to measure flow rate (e.g., urination), temperature or acceleration (e.g., movement and orientation of the patient).

The second implantable device of the present invention is sized for implantation within the patient's vagina. It includes a power source, such as a battery, a pressure sensor, a data storage element, and a data retrieval device, housed within an outer shell. A thin-walled inflatable sleeve or cuff with a seal ring is mounted over the anterior portion of the outer shell of the second implantable device. This inflatable sleeve or cuff is used to securely position the device in the vagina. When pressurized, the sleeve expands radially against the vaginal walls, helping to secure the second implantable device in the correct position. Also, anti-rotational ribbing and/or surface texturing on the inflatable sleeve further assists in maintaining the proper orientation of the second device within the patient's vagina.

Even more preferably, the sleeve has variable thickness walls which, along with the molded ribs, preferentially bias the sleeve to expand radially, with minimal elongation. A small hole in the anterior end of the outer shell provides a pneumatic (or hydraulic) path between the inside of the shell and the inside of the sleeve, ensuring that vaginal or abdominal pressure applied to the sleeve can be detected by a pressure sensor mounted on a printed circuit board inside the outer shell. Preferably, the outer shell is rigid, and the sleeve is formed from silicone or other suitable material for expansion by inflation.

Like the first device, the second implantable device also has a magnet and a coil. Preferably, the outer shell of the second implantable device has a flattened portion near which the magnet and coil are situated, preferably inside the device. The magnet of the second implantable device, when the second device is deployed in the patient's vagina, is of opposite polarity to the magnet in the first implantable device, when the first implantable device is deployed in the patient's bladder, and attracts the magnet of the first implantable device to maintain the first device in proximity to the second device to effect an inductive coupling between the coils of the first and second devices so that the first device may be powered by the power source of the second device without the need for a separate battery being housed within the first device. The omission of a battery allows the first device to be made quite small.

The magnets not only couple the two implantable devices together in proximity to one another, but they also are used to orient the first device in a particular manner. The sensor in the first implantable device, which is used for sensing a physiological property within the bladder, is situated at the opposite side of the housing from where the magnet is situated. Thus, the attraction between the magnets of the first and second implantable devices causes the first implantable device to be oriented in such a way that the device in the patient's bladder is held within the bladder at a particular location, without migrating within the bladder, and is kept with the sensing component end pointed away from the bladder wall, thereby minimizing possible obstruction of the sensing component and inaccurate measurements. Also, slightly negative buoyancy in the first implantable device keeps the first device from floating to the top of the bladder.

As mentioned previously, the first implantable device includes one or more sensing components for sensing a physiological property within the bladder, and a data storage element for storing data representing the physiological properties sensed by the sensor. It does not include a power source, but rather an inductive coil, which is used in conjunction with the second implantable device and is powered by the battery in the second implantable device through the inductive coupling between the two devices.

Preferably, the first implantable device of the present invention has a magnet which is cylindrical in shape that is mounted concentrically within the inductive coil situated in the first device. Both the coil and the magnet are mounted at the posterior end of the first implantable device to ensure that the magnet and coil are held against the bladder wall adjacent or in proximity to the magnet and coil of the second implantable device deployed in the patient's vaginal canal.

The second implantable device receives transmitted data from the first implantable device into its volatile memory. The second device acquires and stores abdominal pressure data or other data sensed by either the first device or the second device.

The urodynamic system of the present invention may further include an external module or data processing unit. This data processing unit receives the stored data from either or both of the first and second implantable devices that is transmitted to the data processing unit for analysis and ultimate treatment of bladder function.

A method for urodynamic evaluation, in accordance with the present invention, includes the steps of deploying a first implantable device within a patient's bladder, the first device including at least one sensor for sensing a physiological property within the bladder and having a first induction coil and a first magnet. The method also includes the step of deploying a second implantable device within the patient's vagina. The second device includes a power source, a second induction coil and a second magnet.

The method further includes the step of magnetically attracting the first magnet of the first implantable device with the second magnet of the second implantable device to maintain the first device in proximity to the second device. This effects an inductive coupling between the first inductive coil of the first device and the second inductive coil of the second device so that the first device may be powered by the power supply situated in the second device, without the need for a separate power source to be housed by the first implantable device.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

The present invention is an improved and robust implantable device and system that effectively captures ambulatory urodynamic data for assessment of urinary incontinence. The system preferably employs Micro Electro-Mechanical System (MEMS) technology, which relates to a class of small devices that integrates tiny mechanical and electrical components on a silicon chip.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to the female urinary system, it is to be understood that it can be readily adapted for use in the male urinary system. Further, the inventive principles, apparatus and methods disclosed herein may also have application to assessing functionality in other areas, such as coronary or pulmonary functionality.

Figure 3:
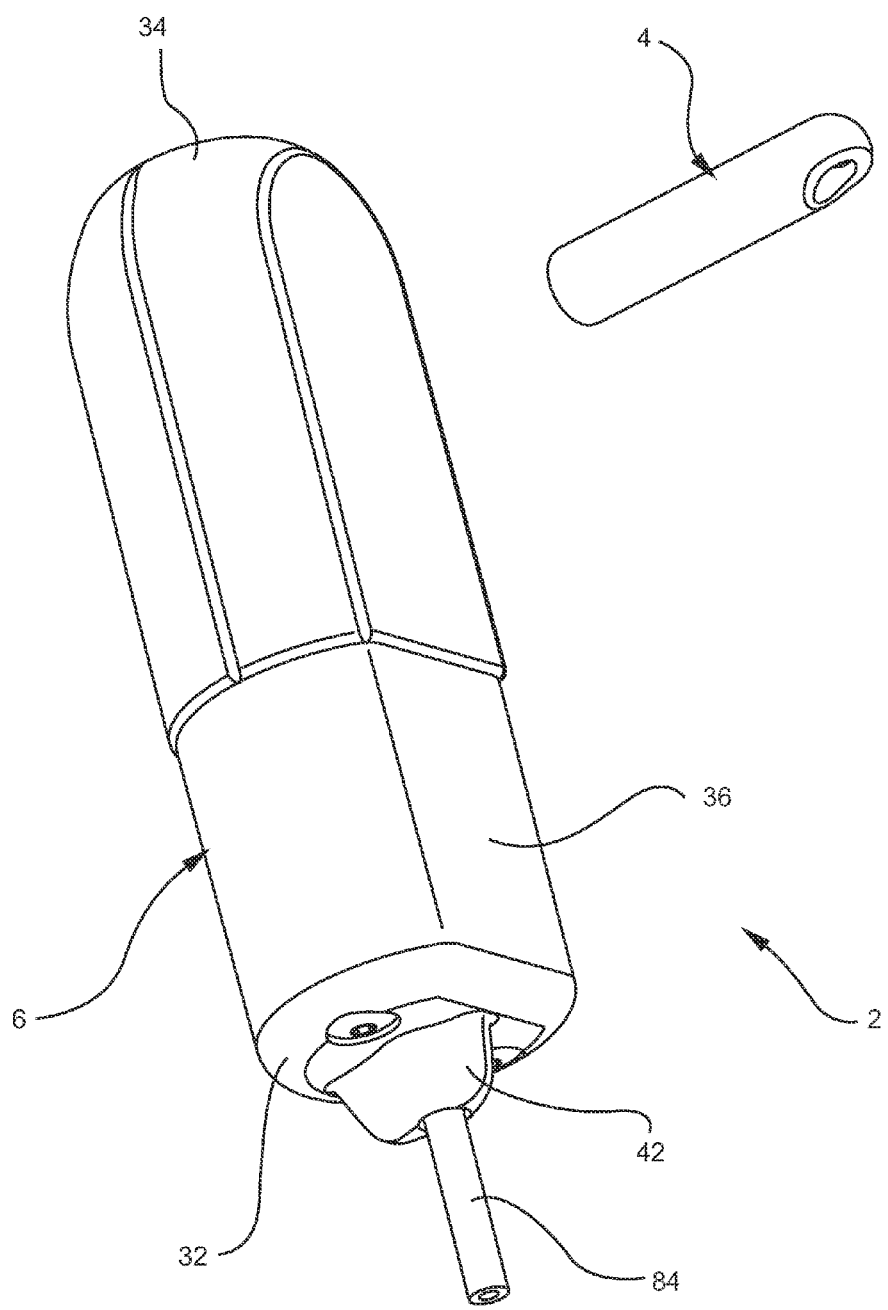
FIG. 3 is an isometric view of the first implantable device and the second implantable device of the urodynamic system of the present invention, and illustrating the preferred operational orientation of the first and second devices.
Figure 4:
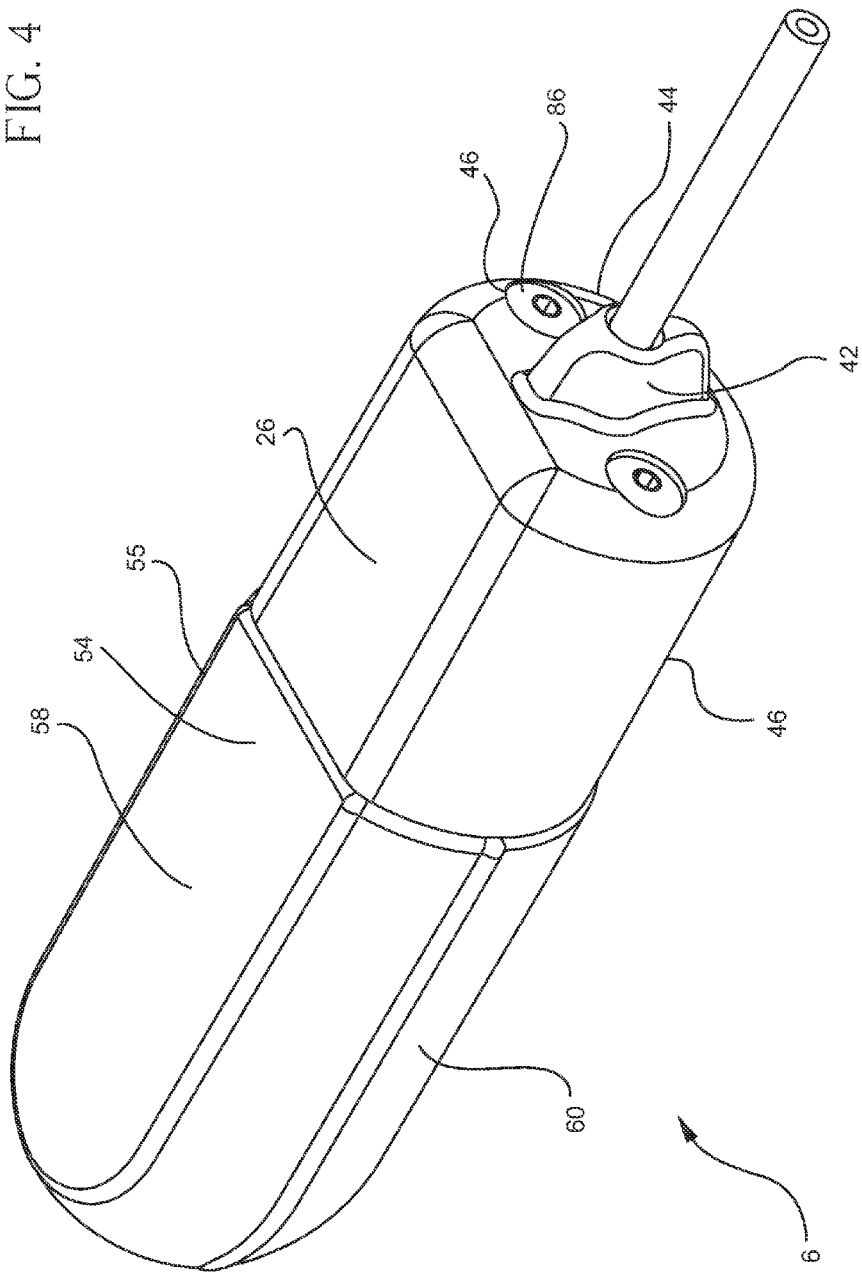
FIG. 4 is an enlarged isometric view of a proximal end portion of the second implantable device of the present invention.

Initially referencing FIG. 3 of the drawings, the present invention is an implantable urodynamic system 2. The implantable urodynamic system 2 includes two implantable devices, a first implantable device 4 and a second implantable device 6. The first implantable device 4 is sized and designed for implantation into a patient's bladder. The second implantable device 6 is specifically sized and designed for implantation into a patient's vagina. The first implantable device 4 and second implantable device 6, operate together to form and define the implantable urodynamic system 2 of the present invention.

Figure 1:
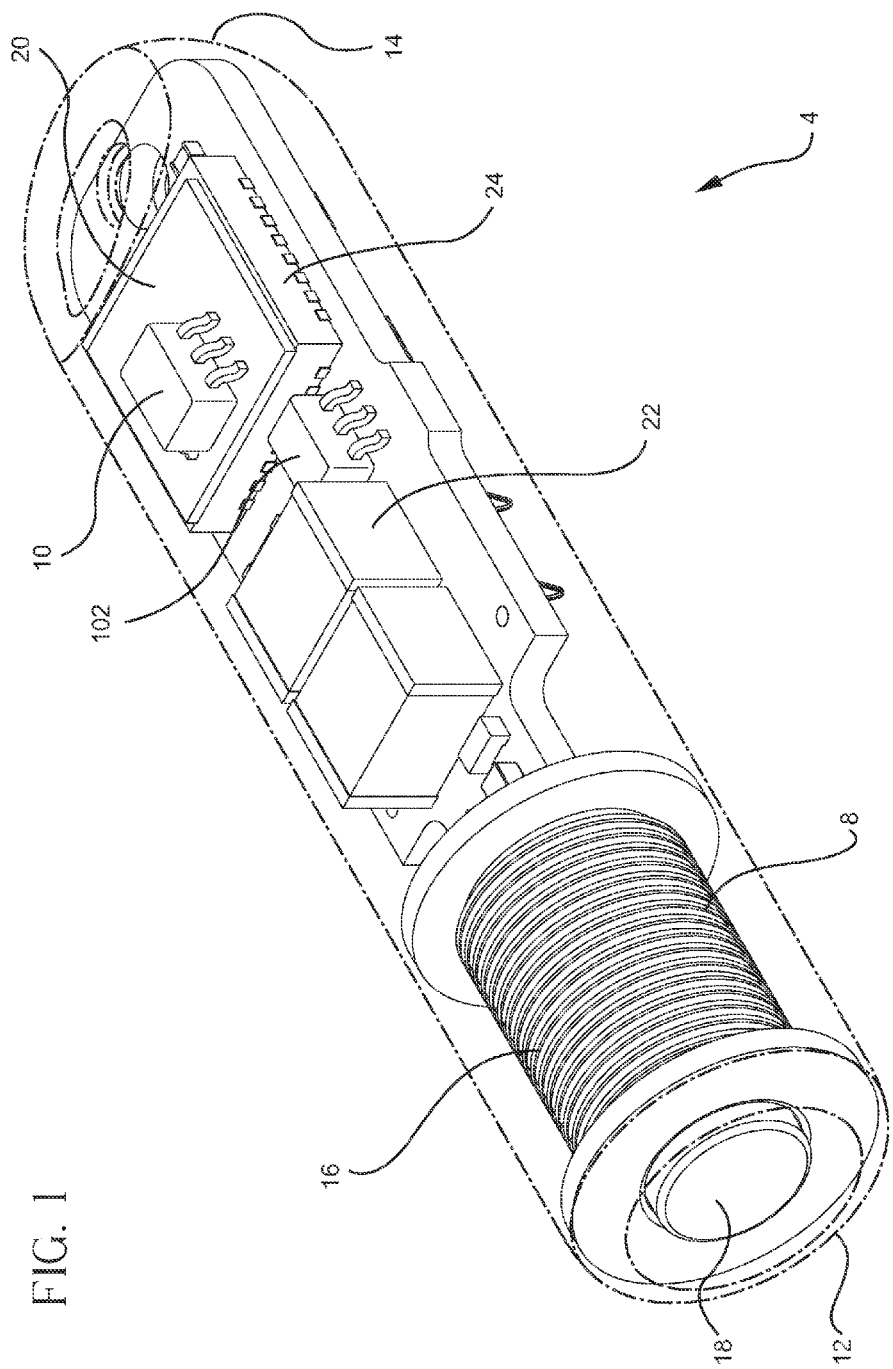
FIG. 1 is an isometric view of one component (i.e., a first implantable device) of an implantable urodynamic system formed in accordance with the present invention, with the outer housing of the first implantable device shown in phantom to view the internal components thereof.
Figure 2:
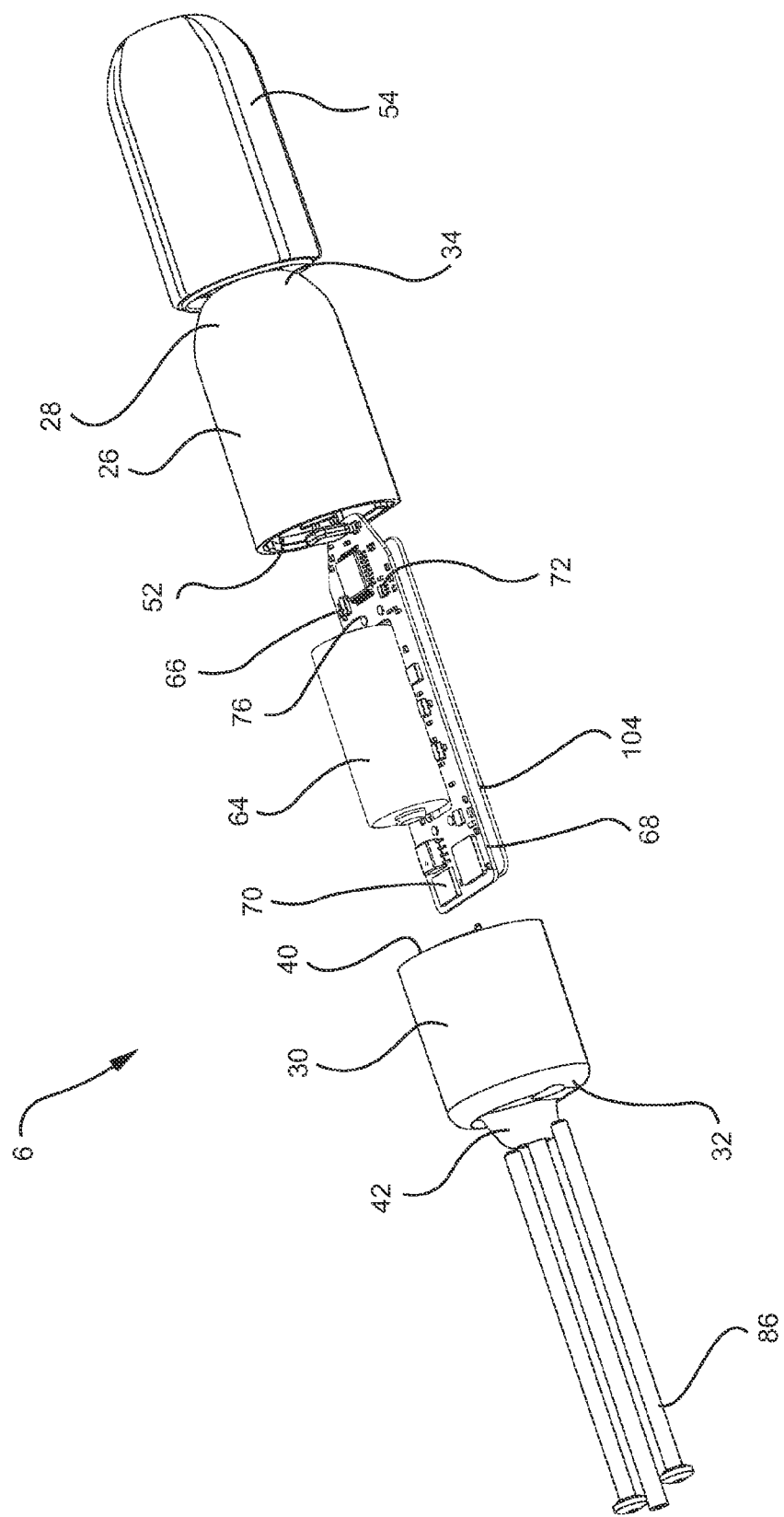
FIG. 2 is an exploded isometric view of another component (i.e., a second implantable device) of an implantable urodynamic system formed in accordance with the present invention.

Now referencing FIG. 1, it will be seen that the first implantable device 4 includes a housing 8 with an internal cavity 10. The housing includes two axial ends: a posterior end 12 and an anterior end 14. An inductive coil 16 is mounted within the internal cavity 10 of the housing 8 at the posterior end 12. Also, a magnet 18 is mounted concentrically with respect to the inductive coil 16 within the internal cavity 10 at the posterior end 12. The first implantable device 4 may also include one or more sensing components 20 for sensing the physiological properties of the bladder, and a data storage element 22 for recording such properties. A printed circuit board 24 is mounted along the axial plane of the first implantable device 4 within the internal cavity 10. The sensing component 20, data storage element 22 and additional electronic components, such as a transmitter 102 which transmits stored physiological data either to the second implantable device or, more generally, to a point outside the bladder, may be secured to the printed circuit board 24, specifically with the sensing component 20 mounted towards the anterior end 14 of the housing 8.

Turning now to FIGS. 2 and 4-6, the second implantable device 6 of the present invention includes an outer shell 26. The outer shell 26 may include a first shell portion 28 and a second shell portion 30 which cooperatively securely mates together. The outer shell 26 may be constructed of a variety of materials but is preferably made of a polycarbonate material. The outer shell 26 has a proximal axial end 32, a distal axial end 34, a ventral surface 36, and an opposite posterior surface 38, and defines an internal cavity 40 for housing electronic components. The outer shell 26 preferably is generally cylindrical in shape; however, the ventral surface 36 is flattened to help ensure its proper orientation with respect to the first implantable device 4. The proximal end 32 of the outer shell 26 is squared off in shape (less rounded than the distal end 34) with a bilaterally flattened tab 42 formed perpendicular to its surface and extending therefrom, which cooperates with a complementary-shaped insertion tool (not shown). The bilaterally flattened tab 42 includes a central bore 44 formed through the thickness of the outer shell and extending into the internal cavity 40 for receiving a pressurization tube 84 for inflating an outer sleeve 54. The proximal end 32 of the outer shell 26 may further include a plurality, but preferably two, casing bores 46 formed through the thickness of the outer shell 26 for receiving casing screws 86.

Figure 5:
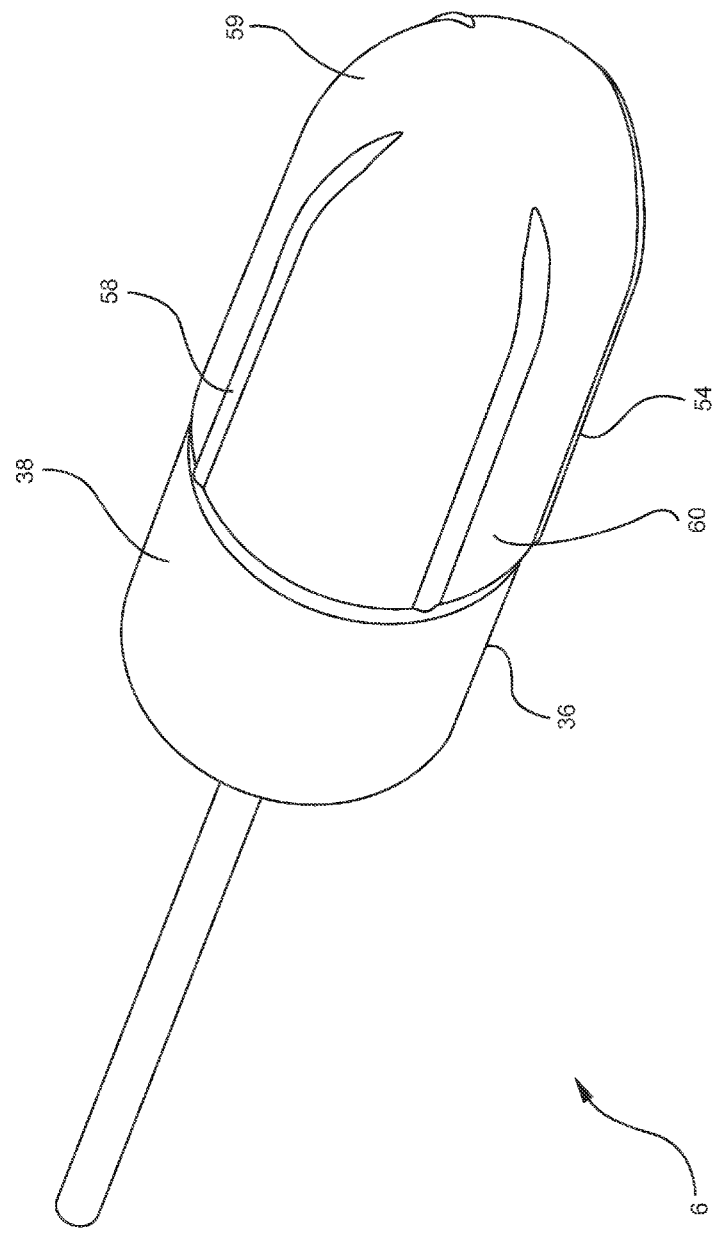
FIG. 5 is an enlarged isometric view of a distal end portion of the second implantable device of the present invention.
Figure 6:
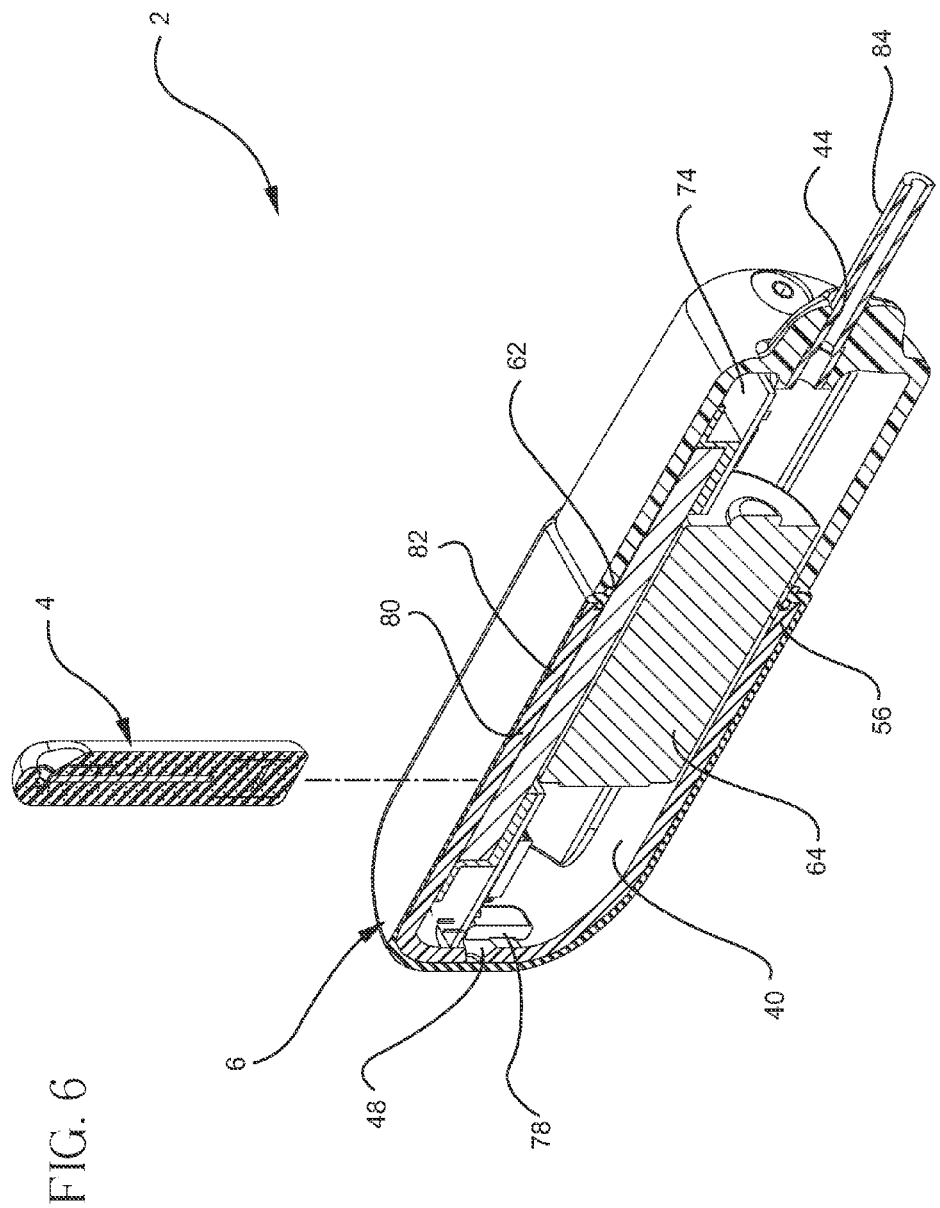
FIG. 6 is a cutaway isometric view of the implantable urodynamic system of the present invention.

As can be seen in FIGS. 5 and 6, the distal end 34 of the outer shell 26 of the second implantable device 6 is generally rounded, but with a flattened axial tip 48. Within the flattened tip 48 is a formed pressure bore 50 through the thickness of the outer shell 26 and into the internal cavity 40. Internally extruded from the outer shell 26 at the distal end 34 is a plurality, but preferably two, internally threaded casing housings 52 that align with the casing bores 46 in the proximal end 32 and which are engaged by the ends of the casing screws 86 when the second implantable device 6 is assembled.

A thin walled inflatable sleeve 54 conforming to the shape of the distal end 34 of the outer shell 26 of the second implantable device 6 is fitted over the distal end 34 of the outer shell 26. The inflatable sleeve 54 has variable thickness walls 55 that direct the sleeve 54 to inflate radially when pressurized and minimize elongation. The sleeve 54 has an inner surface 56, an outer surface 58 and a flattened tip 59. The outer surface 58 of the sleeve 54 may include a plurality of circumferentially spaced apart, radially outwardly extending ribs 60 extending along the length of the sleeve 54 or a portion thereof and/or surface texturing to limit the sleeve's longitudinal extension when inflated and resist rotation of the implantable second device 6 when deployed in the patient's vagina. The sleeve 54 also may include a sealing gasket 62 that is received in a groove situated between the mating edges of the upper and lower shell portions 28, 30 to insure a fluid tight seal between sleeve 54 and shell 26.

The second implantable device 6 may also include a power source 64, such as one or more batteries, a pressure sensor 66, a data storage element 68, and a data retrieval device 70, as well as other electronic components, such as a transmitter 104 that transmits data to a point outside the patient's vagina. A printed circuit board 72 having a bottom side 74 and a top side 76 is mounted along the axial plane of the second implantable device 6 within the internal cavity 40. The power source, preferably a battery 64, a photo diode 78, the pressure sensor 66, the data storage element 68, and the data retrieval device 70 are mounted to the bottom side 74 of the circuit board 72. A magnet 80 and an inductive coil 82 are preferably mounted on the top side 76 of the circuit board 72 facing and in close proximity to the flattened ventral surface 36 of the outer shell 26, with the magnet 80 preferably being disposed concentrically within the confines of the inductive coil 82.

The assembly of the second implantable device 6 is described as follows. The inflatable sleeve 54 is fitted over the first shell portion 28 with the sealing gasket 62 extending over the open end of the first shell portion 28. A pressurization tube 84 is inserted through the central bore 44 of the tab 42. The second shell portion 30 is aligned with the first shell portion 28 and the casing screws 86 are inserted through the casing bores 46 in the second shell portion 30 and into the internally threaded casing housings 52 of the first shell portion 28 to secure the two shell portions together, with the sealing gasket 62 fluidtightly held therebetween.

Now turning to FIGS. 7a-7f, the deployment of the first implantable device 4 and the second implantable device 6 of the urodynamic system of the present invention will be described in detail. The second implantable device 6 is inserted into the vaginal canal 90 with its inflatable sleeve 54 deflated. Once the second implantable device 6 is in a desired position in the vaginal canal, it is inflated by pressurizing the pressure tube 84, which in turn pressurizes the internal cavity 40 of the outer shell 26. Pressure equalizes by exiting the pressure hole 50 in the distal end 34 of the outer shell 26 and into the flattened tip 59 of the inflatable sleeve, causing the radial inflation and expansion of the inflatable sleeve 54, as the air is trapped in the space between the sleeve 54 and the outer shell 26 by the sleeve seal 62. The expansion of the inflatable sleeve 54 secures the second implantable device 6 within the vagina 90.

Figure 7A:
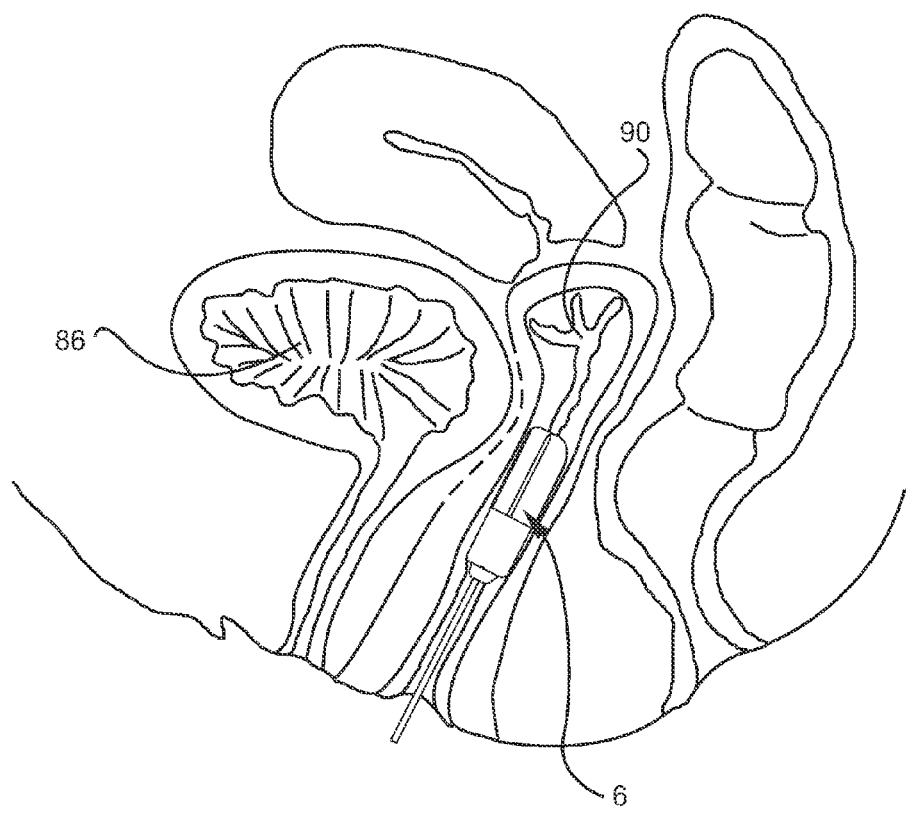
FIG. 7a is a cutaway view of a patient's body and illustrating the second implantable device of the present invention in a first stage of deployment in the vagina of the patient.
Figure 7B:
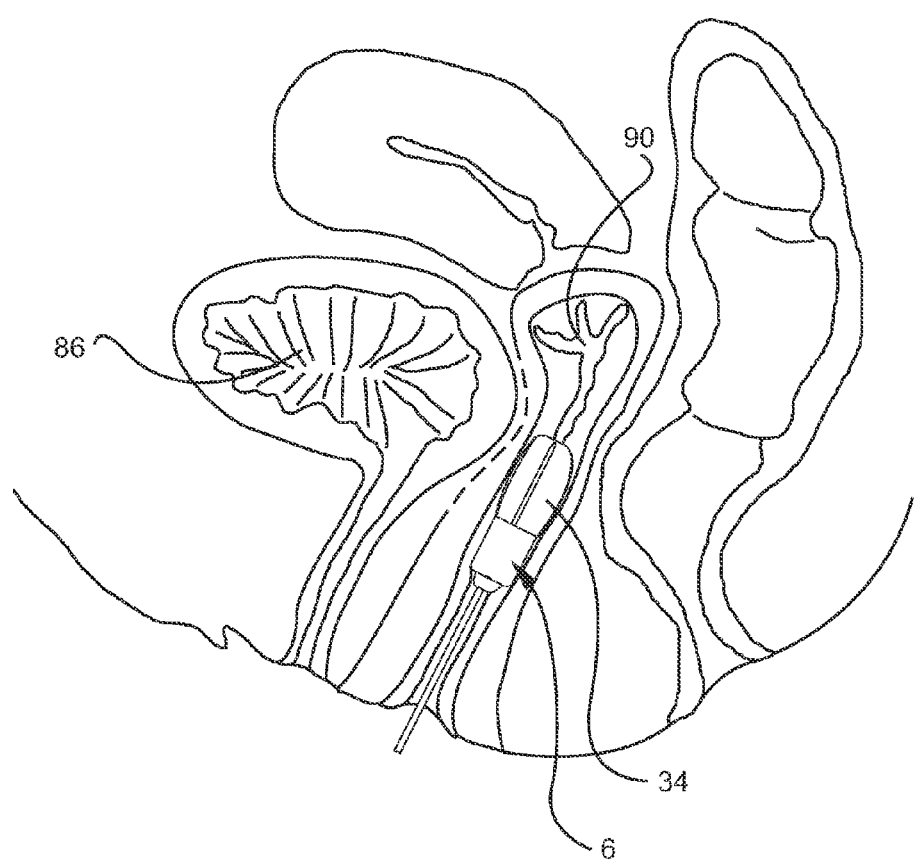
FIG. 7b is a cutaway view of a patient's body and illustrating the second implantable device of the present invention in a second stage of deployment in the vagina of the patient, that is, with the sleeve inflated.
Figure 7C:
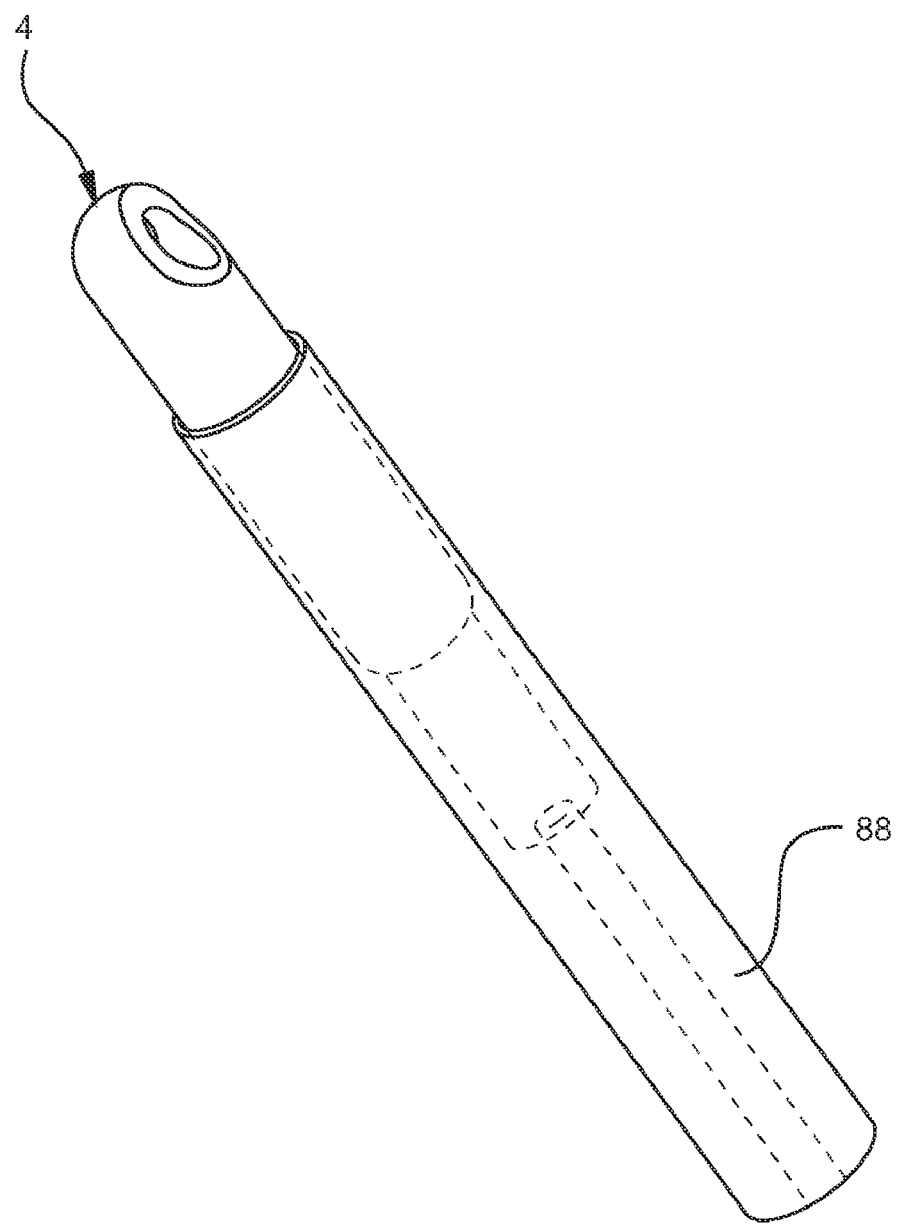
FIG. 7c is an isometric view of the first implantable device of the present invention and an insertion tool used for deploying the first implantable device in a patient's body.
Figure 7D:
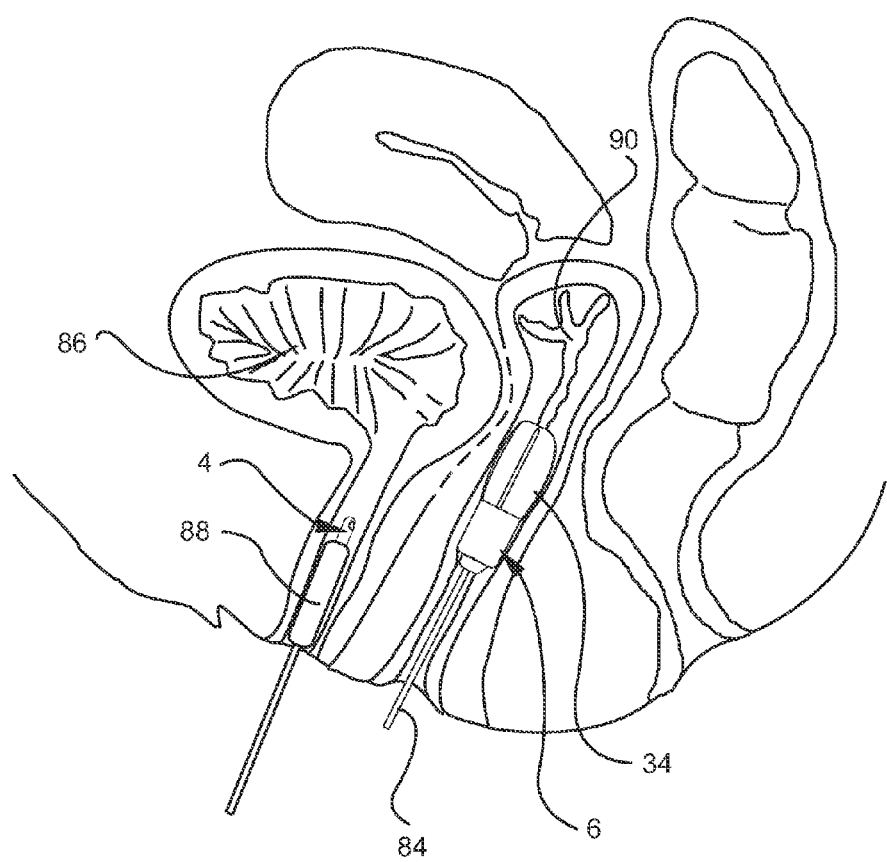
FIG. 7d is a cutaway view of a patient's body and illustrating the first implantable device of the present invention in a first stage of deployment in the bladder of the patient.
Figure 7E:
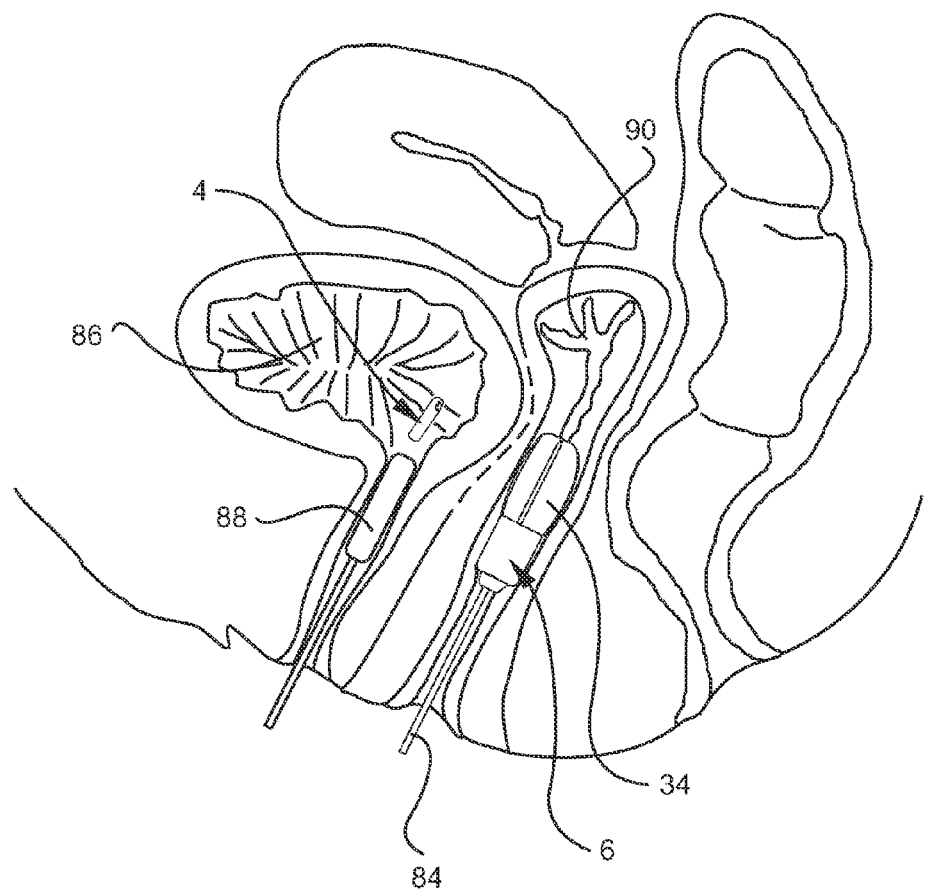
FIG. 7e is a cutaway view of a patient's body and illustrating the first implantable device of the present invention in a second stage of deployment in the bladder of the patient.
Figure 7F:
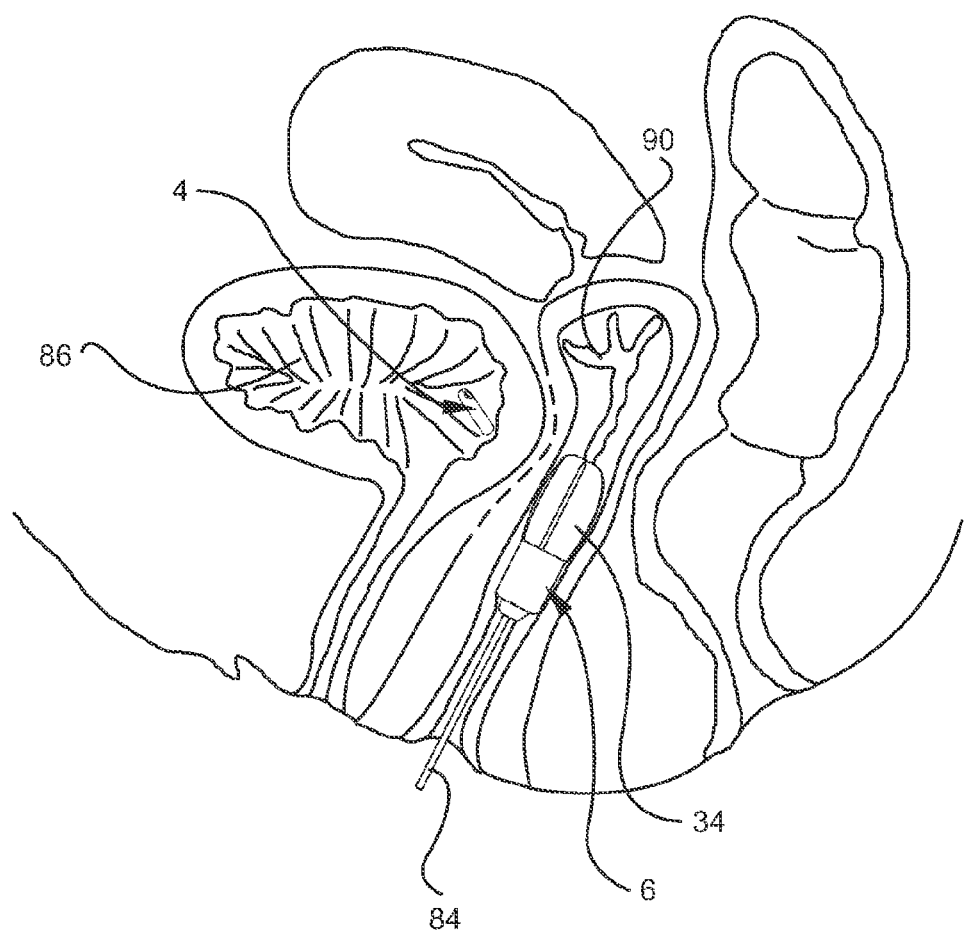
FIG. 7f is a cutaway view of a patient's body and illustrating the first implantable device and the second implantable device of the implantable urodynamic system of the present invention deployed respectively in the bladder and vagina of the patient.

The first implantable device 4 is implanted into the bladder 87 through the urethra using an insertion tool 88. As illustrated in FIG. 7f, once both devices are implanted, the magnet 18 in the posterior end 12 of the first implantable device 4 is attracted to the magnet 80 of opposite polarity located in proximity to the ventral surface 36 of the second implantable device 6. The magnetic attraction between the first and second devices 4, 6 keeps the devices in close proximity to each other and properly oriented to effect an inductive coupling between the coils 16, 82 of the two devices. The electronics of the first implantable device 4 are powered by the power source 64 of the second implantable device 6 by using the inductive coupling between the inductive coil 16 located within the posterior end 12 of the first implantable device 4 and the inductive coil 82 in proximity to the ventral surface 36 of the second implantable device 6.

During operation, the location of the magnet 18 in the posterior end 12 of the first implantable device 4 insures that the posterior end 12 is held against the bladder 87, adjacent or in close proximity to the magnet 80 in the second implantable device 6. Additionally, the location of the magnet 18 points the sensing component 20 away from the wall of the bladder 87, thereby minimizing possible obstructions and erroneous data measured by the sensing component. The first implantable device 4 of the present invention also exhibits a negative buoyancy to help keep the device 4 from floating to the top of the bladder 87. The first implantable device 4 can be used to measure and transmit a variety of data, including but not limited to bladder pressure, temperature data, urination flow rate, and patient acceleration. These measurements can be performed while the patient remains ambulatory.

The second implantable device 6 can also be used to measure, transmit and store a variety of data, including abdominal and vaginal pressures. The second device 6 also receives the transmitted data from the first implantable device and stores it in its storage element 68. All the data stored in the second implantable device 6 can be transmitted to an external module or circuit 100 for analysis and corresponding treatment of a bladder condition, in the same or similar manner as that known to one skilled in the art, such as described in the aforementioned Tracey et al. U.S. patent application Ser. No. 11/043,830.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A urodynamic system, which comprises:
   a first implantable device sized for implantation within a patient's bladder, the first implantable device including a housing having a first end, a second end, and a longitudinal axis extending between the first and second ends, the first implantable device including at least one sensor for sensing a physiological property within the bladder, the first implantable device having mounted thereon a first inductive coil and a first magnet, wherein the first magnet is located at the first end of the housing of the first implantable device and the at least one sensor is located at the second end of the housing of the first implantable device; and
   a second implantable device sized for implantation within the patient's vagina, the second implantable device including a power source and the second implantable device having mounted thereon a second inductive coil and a second magnet;
   the first magnet of the first device being magnetically attractable to the second magnet of the second device to hold the first end of the housing of the first implantable device against a wall of the bladder and orient the at least one sensor at the second end of the housing of the first implantable device away from the wall of the bladder for minimizing obstruction of the at least one sensor and to maintain the first device in proximity to the second device to effect an inductive coupling between the first inductive coil of the first device and the second inductive coil of the second device when the first and second devices are respectively implanted in the patient's bladder and vagina.

2. A urodynamic system as defined by claim 1, wherein the first end of the housing defines a flat end surface, and wherein the first magnet, the first inductive coil and the at least one sensor are disposed within the housing of the first implantable device.

3. A urodynamic system as defined by claim 2, wherein the first inductive coil is situated near the first end of the housing of the first implantable device.

4. A urodynamic system as defined by claim 1, wherein the first implantable device includes a data storage element for storing data representing the physiological property sensed by the at least one sensor.

5. A urodynamic system as defined by claim 4, wherein the at least one sensor of the first implantable device senses bladder pressure.

6. A urodynamic system as defined by claim 1, wherein the first magnet of the first implantable device is cylindrical in shape, and wherein the first inductive coil is concentrically disposed about the cylindrically-shaped first magnet.

7. A urodynamic system as defined by claim 1, wherein the first implantable device exhibits a negative buoyancy.

8. A urodynamic system as defined by claim 1, wherein the first implantable device includes a data transmission device for transmitting data representing the sensed physiological property to a point external of the patient's bladder.

9. A urodynamic system as defined by claim 1, wherein the second implantable device includes an inflatable sleeve mounted thereon.

10. A urodynamic system as defined by claim 1, wherein the second implantable device includes an outer shell having a cylindrical shape and a flat side surface, and an inflatable sleeve mounted on the outer shell and covering at least a portion of the outer shell, the outer shell and inflatable sleeve together defining a fluidtight space therebetween for receiving a fluid under pressure to effect the inflation of the sleeve.

11. A urodynamic system as defined by claim 10, wherein the inflatable sleeve has an outer surface and includes an anti-rotational structure situated thereon, and wherein the inflatable sleeve has variable thickness walls that direct radial inflation and minimize longitudinal inflation of the inflatable sleeve.

12. A urodynamic system as defined by claim 11, wherein the anti-rotational structure includes a plurality of radially outwardly extending ribs situated on the outer surface, the ribs being spaced apart from one another about the periphery of the outer surface.

13. A urodynamic system as defined by claim 11, wherein the anti-rotational structure includes surface texturing on the outer surface.

14. A urodynamic system as defined by claim 10, wherein the sleeve includes an outer wall, the outer wall having at least first and second portions, the thickness of the outer wall of the first portion being greater than the thickness of the outer wall of the second portion to effect more expansion of the sleeve in proximity to the second portion than in proximity to the first portion when the sleeve is inflated.

15. A urodynamic system as defined by claim 10, wherein the second implantable device includes a pressure sensor in fluid communication with the fluidtight space between the outer shell and the inflatable sleeve to detect one of a vaginal pressure and abdominal pressure applied to the sleeve when the second device is implanted in the patient's vagina.

16. A urodynamic system as defined by claim 10, wherein the second implantable device includes the outer shell, the outer shell having the flat side surface, the second inductive coil and the second magnet being situated in proximity to the flat side surface, wherein the inflatable sleeve has ribs that extend along a length of the sleeve for resisting rotation of the second implantable device when deployed in the patient's vagina and for orienting the flat side surface of the outer shell with respect to the first implantable device.

17. A urodynamic system as defined by claim 1, wherein the second implantable device includes a data storage element situated thereon.

18. A urodynamic system as defined by claim 1, wherein the second implantable device includes a data transmission device situated thereon for transmitting data to a point external of the patient's vagina.

19. A urodynamic system as defined by claim 1, which further comprises:
a data processing unit, the data processing unit being operatively linked to at least one of the first implantable device and the second implantable device, the data processing unit being positionable outside the patient's body.

20. A urodynamic system, which comprises:
a first implantable device implantable in a first organ of a patient, the first implantable device having a housing with an anterior end, a posterior end, and a longitudinal axis extending between the anterior and posterior ends, the first implantable device including at least one sensor located at the anterior end of the housing for sensing a physiological property relating to the first organ, the first implantable device having mounted thereon a first inductive coil and a first magnet located at the posterior end of the housing; and
a second implantable device for implantation within a second organ of the patient, the second implantable device including a power source and the second implantable device having mounted thereon a second inductive coil and a second magnet;
the first magnet of the first implantable device being magnetically attractable to the second magnet of the second implantable device to maintain the posterior end of the housing of the first implantable device in proximity to the second implantable device to orient the at least one sensor at the anterior end of the housing of the first implantable device away from the second implantable device for minimizing obstruction of the at least one sensor and to effect an inductive coupling between the first inductive coil of the first implantable device and the second inductive coil of the second implantable device when the first and second implantable devices are respectively implanted in the patient's first organ and second organ, wherein the inductive coupling enable the first implantable device to be powered by the power source of the second implantable device without the need for a separate power source to be connected with the first implantable device.

21. A urodynamic system as defined by claim 20, wherein the magnetic attraction between the first and second magnets holds the first end of the housing of the first implantable device against a wall of the first organ so as to orient the at least one sensor at the second end of the housing of the first implantable device away from the wall of the first organ.

* * * * *